US00PP16267P2

(12) United States Plant Patent
Olesen et al.

(10) Patent No.: US PP16,267 P2
(45) Date of Patent: Feb. 21, 2006

(54) ***CLEMATIS* PLANT NAMED 'EVIPO018'**

(50) Latin Name: *Clematis viticella*
Varietal Denomination: Evipo018

(75) Inventors: Mogens N. Olesen, Fredensborg (DK); Raymond J. Evison, St. Sampsons (GB)

(73) Assignees: Poulsen Roser A/S, Fredensborg (DK); Raymong J. Evison, Ltd., Guernsey (GB)

( * ) Notice: Subject to any disclaimer, the term of this patent is extended or adjusted under 35 U.S.C. 154(b) by 28 days.

(21) Appl. No.: 10/798,699

(22) Filed: Mar. 10, 2004

(51) Int. Cl.
*A01H 5/00* (2006.01)

(52) U.S. Cl. ..... Plt./228

(58) Field of Classification Search ..... Plt./228
See application file for complete search history.

*Primary Examiner*—Kent Bell

(57) ABSTRACT

A new *Clematis* cultivar which is well suited to propagation in glasshouses. With a compact growth habit, profuse, red-purple flowers, and recurrent flowering habit. The variety successfully propagates from softwood cuttings and is suitable for cultivation in commercial glasshouses. This new and distinct variety has shown to be uniform and stable in the resulting generations from propagation.

1 Drawing Sheet

Botanical classification: Genus—*Clematis*. Species—*viticella*.

Variety denomination: 'Evipo018'.

Commercial classification: Early Flowering—Large Flower Cultivar.

SUMMARY OF THE INVENTION

The present invention constitutes a new and distinct variety of *Clematis* which originated from a controlled crossing between the female parent, an unnamed, non-patented seedling and the male parent, an unnamed, non-patented seedling.

The new *Clematis* may be distinguished from its female seed parent by the following characteristic:

While the seed parent has pink flowers 'Evipo018' has red-purple flowers.

The new *Clematis* may be distinguished from its male pollen parent by the following characteristics:

While the pollen parent achieves an average season's growth of 2 to 2.5 meters, 'Evipo018' normally produces 1.5 to 2 meters of growth in one season.

The two parents were crossed and the resulting seed was planted in a controlled environment. The new variety is named 'Evipo018'.

The objective of the hybridization was to create a new and distinct variety for commercial glasshouse and nursery culture with unique qualities such as:

1. Medium sized red-purple flowers;
2. Compact growth habit;
3. Yellow flower center;
4. Attractive "tulip like" initial opening of the flower bud.

These qualities required improvement in *Clematis* varieties that were in commercial cultivation and the objectives have been substantially achieved in the new variety, as evidenced by the unique combination of characteristics that are present in 'Evipo018' which distinguish it from all other varieties of which we are aware.

The seeds from the aforementioned hybridization were germinated and evaluations of the resulting seedling plants were conducted in a controlled environment. As a result, 'Evipo018' was selected by Raymond J. Evison and Mogens N. Olesen in their *Clematis* development program in Domarie Vineries Les Sauvagees, St. Sampsons, Guernsey, Channel Islands, United Kingdom in April 1998.

Asexual reproduction of 'Evipo018' by cuttings was first done by Raymond J. Evison and Mogens N. Olesen in Domarie Vineries Les Sauvagees, St. Sampsons, Guernsey, Channel Islands, United Kingdom in May 1998. This initial and subsequent propagations have demonstrated that the characteristics of 'Evipo018' are true to type and are transmitted from one generation to the next.

BRIEF DESCRIPTION OF THE DRAWING

The accompanying color illustration show as true as is reasonably possible to obtain in color photographs of this type:

FIG. 1.1 Bloom, upper side;

FIG. 1.2 Bloom, lower side;

FIG. 1.3 Mature leaf;

FIG. 1.4 Flower bud ¼ open;

FIG. 1.5 Flower bud attached to stem with juvenile leaves;

FIG. 1.6 Stem showing attachment of leaflets, and juvenile growth.

DETAILED DESCRIPTION OF THE VARIETY

The following is a detailed description of 'Evipo018', as observed in its growth throughout the flowering period in glasshouses at Domarie Vineries Les Sauvagees, St. Sampsons, Guernsey, Channel Islands, United Kingdom. Observed plants were cultivated for a period of 24 months in 2 liter containers under normal glasshouse conditions. Certain phenotypical characteristics of the variety may vary under different environmental, cultural, agronomic, seasonal, and climatic conditions. Color references are made using The Royal Horticultural Society (London, England) Colour Chart, 1995.

For a comparison, the nearest existing *Clematis* variety is 'Evifive', a patented variety described and illustrated in U.S. Plant Pat. No. 10,913 issued May 25, 1999. Chart 1 details several physical characteristics of 'Evipo018' and the comparison variety.

CHART 1

| | 'Evipo018' | 'Evifive' |
|---|---|---|
| Leaflet Size | 50 mm wide | 30 mm wide |
| Typical season's growth | 1.5 to 2 meters | 2 to 2.5 meters |
| Flower Size | 100 to 120 mm | 150 to 180 mm |

FLOWER AND FLOWER BUD

Blooming habit: Recurrent. Flowering period is normally May to June, and August to September.

Flower bud:

*Size.*—30 to 50 mm in length. Bud diameter is 10 to 20 mm.

*Bud form.*—Long ovoid.

*Bud color.*—Red-Purple Group 61A at ¼ opening.

Peduncle:

*Surface.*—Smooth.

*Length.*—90 to 120 mm average length.

*Diameter.*—2.5 mm.

*Color.*—Green Group 137B.

*Strength.*—Strong. Erect.

Receptacle: None observed.

Flower arrangement:

*Borne.*—Singly.

Flower bloom:

*Size.*—100 to 120 mm in diameter. 45 mm in depth.

*Profile.*—Upon opening, flowers are flat to concave, with slightly reflexing tepals.

*Tepal color.*—Upon opening: Upper surface is Red-Purple Group 71A. The reverse side is Red-Purple Group 71A. A central bar, the color of Red-Purple Group 72B extends the length of the tepal on both the upper and lower surfaces. After opening: Upper surface is Red-Purple Group 71A. The reverse side is Red-Purple Group 72A. A central bar, the color of Red-Purple Group 72B extends the length of the tepal on both the upper and lower surfaces.

*Variations.*—At the base, tepals are Red-Purple Group 61A and White Group 155A.

*General tonality.*—Red-Purple Group 71A.

*Fragrance.*—None to very light floral scent.

*Lasting quality on plant.*—5 to 10 days.

*Lasting quality as a cut flower.*—1 to 3 days.

Tepals:

*Quantity.*—Single. Six tepals on average.

*Size.*—80 to 90 mm in length by 30 to 40 mm wide.

*Shape.*—Individual tepal shape is obovate.

*Cross section.*—Reflexed.

*Margins.*—Entire.

*Undulation of margin.*—Absent.

*Tepal apex.*—Cuspidate.

*Tepal base.*—Acute.

*Recurvature of tip.*—Slight.

*Arrangement.*—Tepals are arranged regularly.

Reproductive organs:

*Arrangement.*—Open.

*Pollen.*—Quantity: Abundant. Color: Yellow Group 11B.

*Anthers.*—Size: 4 to 7 mm in length. Color: Yellow Group 11B. Quantity: 80 (actual count).

*Filaments.*—Color: White Group 155A. Length: 12 mm.

*Pistils.*—Color: Yellow Group 11B. Quantity: 50 to 70.

*Stigmas.*—As the flower ages, stigmas increasingly protrude from the anthers and filaments.

*Styles.*—Color: Yellow Group 11B.

PLANT

Plant form: Climbing and spreading.

Plant growth: Moderately vigorous.

Size: Seasons growth attains 1.5 to 2 meters in height. Average spread is 0.75 meters.

Hardiness: Trials to date show the variety hardy in USDA Zones 4–9.

Stems:

*Color.*—Young wood: Green Group 138A with intonations of Greyed-Purple 183C. Older wood: Greyed-Orange Group 165C.

*Internodes.*—Shape: Cylindrical. Length: 100 to 120 mm.

*Surface.*—Young wood: Smooth. Older wood: Smooth.

*Stem length.*—70 to 120 cm from the base of the plant to the flowering portion.

*Stem diameter.*—2.5 to 3 mm.

Plant foliage:

*Leaf characteristics.*—Deciduous.

*Mature leaf form.*—Pinnate. There are 3 leaflets on average.

*Compound leaf size.*—Mature compound leaves are 180 to 210 mm in length by 150 to 180 mm wide.

*Color.*—Upper surfaces of mature leaves are Green Group 137B. Lower surfaces are Green Group 137B.

Plant leaves and leaflets:

*Petioles.*—Size: Average length: 60 to 80 mm. Color: Green Group 137B. Clasping: By leaf petiole. Surface texture underneath: Smooth.

*Petioloule.*—Length: 40 to 50 mm. Diameter: 1 mm. Color: Greyed-Purple Group 183B.

*Stipules.*—Absent.

*Leaflet shape.*—Base: Rounded to cordate. Apex: Acute.

*Margin.*—Entire.

*Leaflet size.*—80 mm (l)×50 mm (w).

*Texture.*—Upper Surface: Rough. Matte appearance. Lower Surface: Rough. Glossy appearance.

*Thickness.*—Moderate.

Disease resistance: Subject to any disease that normally attacks the species, however the variety is more tolerant to mildew than some *Clematis*.

It is claimed:

1. A new and distinct variety of *Clematis* plant named 'Evipo018', as illustrated and described herein due to its abundant red-purple flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

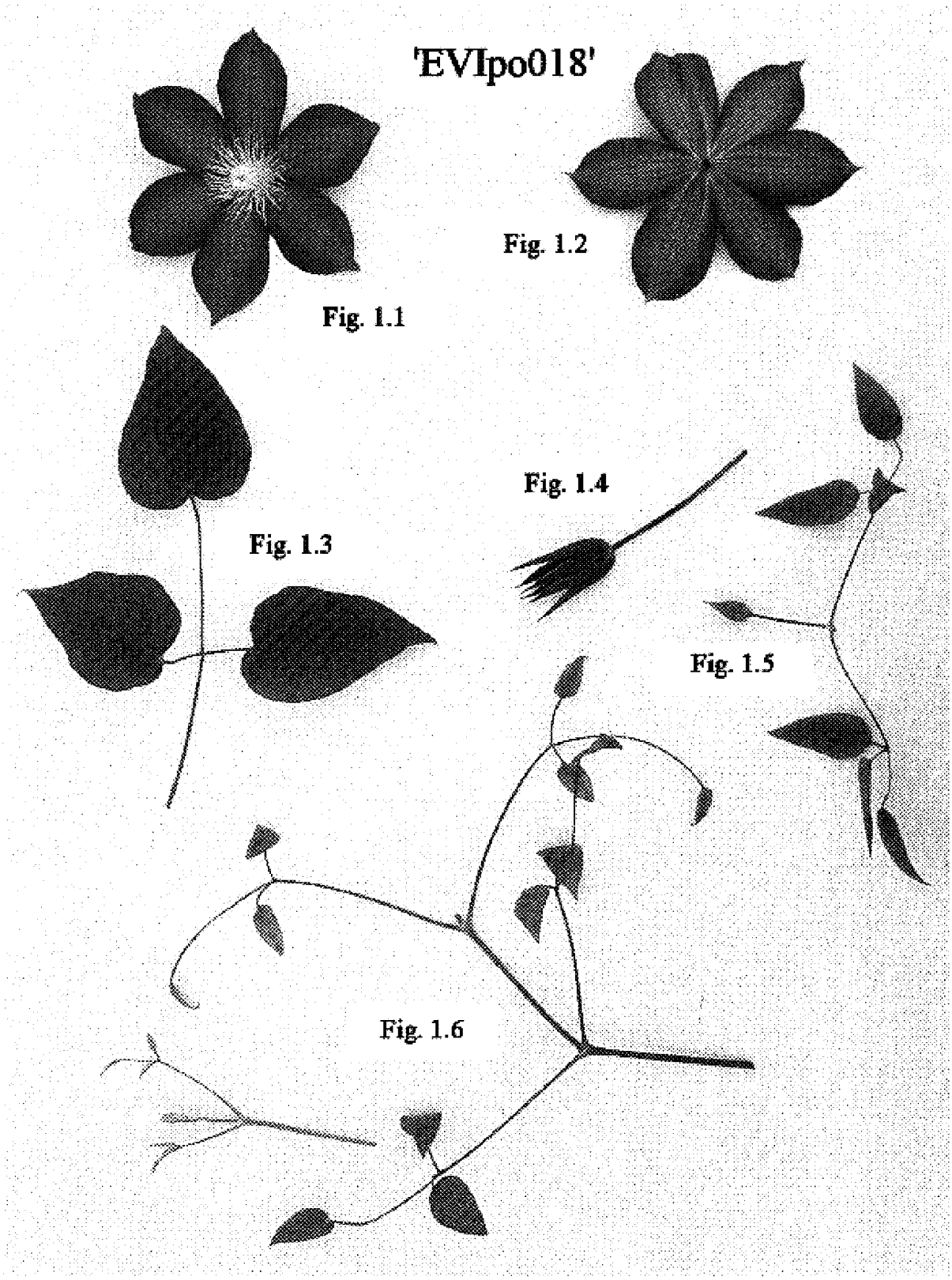
'EVIpo018'
Fig. 1.1
Fig. 1.2
Fig. 1.3
Fig. 1.4
Fig. 1.5
Fig. 1.6